United States Patent [19]
Dillow et al.

[11] Patent Number: 6,149,864
[45] Date of Patent: Nov. 21, 2000

[54] SUPERCRITICAL FLUID STERILIZATION METHOD

[75] Inventors: Angela K. Dillow, Minneapolis, Minn.; Robert S. Langer, Newton, Mass.; Neil Foster, Ortarmon, Australia; Jeffrey S. Hrkach, Somerville, Mass.

[73] Assignee: Massachusetts Institute of Technology, Cambridge, Mass.

[21] Appl. No.: 09/104,775

[22] Filed: Jun. 25, 1998

[51] Int. Cl.[7] ............................................. A61L 2/00
[52] U.S. Cl. ............................ 422/28; 422/32; 422/33
[58] Field of Search .................................. 422/4, 28, 29, 422/32, 33, 38, 292, 295, 305, 307

[56] References Cited

U.S. PATENT DOCUMENTS

| | | | |
|---|---|---|---|
| 4,263,253 | 4/1981 | Pilz et al. ..................................... | 422/1 |
| 4,348,357 | 9/1982 | Bithell ....................................... | 422/33 |
| 4,687,635 | 8/1987 | Kaehler et al. ............................. | 422/33 |
| 5,073,203 | 12/1991 | Al-Ghatta .................................. | 422/33 |
| 5,213,660 | 5/1993 | Hossain et al. ............................. | 162/5 |
| 5,723,012 | 3/1998 | Fages et al. ................................ | 623/16 |
| 5,725,579 | 3/1998 | Fages et al. ................................ | 623/16 |
| 5,869,123 | 2/1999 | Osajima et al. ........................ | 426/330 |
| 5,877,005 | 3/1999 | Castor et al. ........................ | 435/286.1 |

FOREIGN PATENT DOCUMENTS

| | | |
|---|---|---|
| 39 04 513 A1 | 8/1990 | Germany . |
| WO 97/48848 A1 | 12/1997 | WIPO . |

OTHER PUBLICATIONS

Lin, et al., "Inactivation of Saccharomyces cerevisiae by supercritical and subcritical carbon dioxide," *Biotechnol. Prog.* 8:458–461 (1992).

Primary Examiner—Krisanne Thornton
Attorney, Agent, or Firm—Arnall Golden & Gregory, LLP

[57] ABSTRACT

A method is provided for sterilizing materials, particularly polymers, for drug delivery and implantation, wherein the material is treated with supercritical fluid carbon dioxide at pressures in the range of 2000 to 3000 psi (140 to 210 bar) and temperatures preferably between 30 and 45° C. for periods between 20 minutes and six hours, more preferably between 0.5 and 2 hours. Agitation, pressure cycling, and the presence of water were found to enhance the sterilization method, which promotes diffusion of the supercritical fluid carbon dioxide into the cells of the microorganism to thereby alter the pH within the cells, killing them. The magnitude and frequency of the pressure cycling, as well as the process time and temperature, may vary according to the type and form of the material to be sterilized and the type of organisms to be killed.

5 Claims, 3 Drawing Sheets

SUPERCRITICAL FLUID STERILIZATION METHOD

BACKGROUND OF THE INVENTION

This invention generally relates to the sterilization of materials, especially polymeric materials for use in biomedical applications, such as polymeric particles for drug delivery or polymeric implants.

The use of polymeric materials in biomedical applications is a rapidly developing technology, especially the use of polymeric particles in controlled drug delivery. Sterilization of these particles is essential to their safe use in vivo. The most common methods for sterilization employ ethylene oxide, UV-radiation, γ-irradiation, or superheated steam. Each of these methods possess certain disadvantages if applied to sterilization of materials for biomedical applications. For example, ethylene oxide residual gas may remain in the material, which can cause hemolysis (Clark, et al., *J. Surg.* 36 (1966); Nair, *J. Biomat. Appl.*, 10:121 (1995)) or other toxic reactions. Other solvents, whether employed as a sterilant or merely as a process medium, similarly may leave residues that must be removed prior to use in a human. Gamma radiation may damage polymers, for example, by altering their shear and tensile strength, or elasticity. The use of UV- or γ-radiation or high temperatures (as, for example, during autoclaving) also may reduce the quality of encapsulated drug or other labile biological materials, especially labile protein drugs, by decreasing bioavailability or by modifying chemical groups to decrease bioactivity.

Hydrostatic pressure (1200–8000 bar) has been used to mechanically rupture yeast cells and spores, as shown, for example, in Hayakawa, et al., *J. Food Sci.*, 59:159 (1994); Hayakawa, et al., *J. Food Sci.*, 59:164 (1994); and Hashizume, et al., *Biosci. Biotech. Biochem.*, 59:1455 (1995). However, hydrostatic pressure coupled with very high shearing forces and high temperatures has met with limited success in sterilizing samples highly contaminated with spores. Konig, et al., "Autosterilization of Biodegradable Implants by Injection Molding Process", *J. Biomed. Mater. Res.*, 38:115–19 (1997). The use of hydrostatic pressures at these magnitudes requires specially designed equipment capable of withstanding such pressures. This equipment generally is more costly to purchase and maintain than lower pressure operating systems. Extremely high pressures may also irreversibly deform some polymeric materials, which would be undesirable for many biomedical applications of these material.

High pressure or supercritical fluids, such as carbon dioxide, have been studied for use in sterilization of food. For example, Haas, et al., "Inactivation of Microorganisms by Carbon Dioxide Under Pressure," *J. Food Safety*, 2:253–65 (1989) describes numerous experiments using high pressure carbon dioxide (up to 900 psig (6 MPa)) to treat food products and several types of microorganisms. However, only up to four orders of magnitude reduction in living cells was provided with most of the microorganisms tested, i.e., complete sterilization was not achieved. Similarly, Kamihira, et al., "Sterilization of Microorganisms with Supercritical Carbon Dioxide," *J. Biol. Chem.* 51(2):407–12 (1987) describes efforts to sterilize microorganisms using supercritical carbon dioxide. However, sterilization of bacillus was not achieved. Nor was sterilization of a microorganism concentration of at least $10^6$ CFU/ml (colony forming units per milliliter) achieved as generally required in standard sterilization tests. See, e.g., König, et al., "Autosterilization of Biodegradable Implants by Injection Molding Process", *J. Biomed. Mater. Res.*, 38:115–119 (1997); Dempsey, et al., "Sterilization of Medical Devices: A Review", *J. Biomat. Appl.* 3:454–523 (1989). König teaches that "the target range of contamination of $1 \times 10^5$ to $5 \times 10^6$ spores/g granules is comparable to the number of spores present on commercially available Paper Strip Biological Indicators used to qualify, validate, and monitor steam sterilization cycles" (p. 118). Similarly, Dempsey teaches using a "standardized challenge of $10^6$ bacillus subtilis spores" to evaluate sterilization efficiency (p. 463).

Supercritical fluid sterilization also has been explored in nonfood applications. U.S. Pat. No. 5,043,280 to Fischer, et al. describes the use of supercritical gases to sterilize polymeric carriers. However, the method disclosed therein uses organic solvents, which could be the actual sterilant and will leave solvent residues in the polymeric materials. Fischer also disclosed treating polymers for long periods of time (e.g., 12 hours) and at high temperatures (e.g., 50° C.), conditions that may damage encapsulated biological materials. More importantly, Fischer began with a microorganism concentration of only $10^4$ CFU/ml, which is below the $10^6$ CFU/ml used in standard sterilization tests.

Some researchers claim to have achieved "sterilization" of several bacterial microbes using carbon dioxide based on only 2 to 3 log order microbial reduction, for example, starting with $10^8$ CFU/ml of bacterial cells and obtaining $10^6$ or $10^5$ CFU/ml viable cells following treatment, which would be reported as 99% or 99.9% inactivation. In contrast, standard sterilization tests generally (as described above) require that at least $10^6$ colony forming units per milliliter (CFU/ml) of starting material be used and that sterilization requires complete inactivation of these cells.

It is therefore an object of the present invention to provide a method and an apparatus to sterilize polymeric materials for use in biomedical applications, in the substantial absence of organic solvents and at relatively low temperatures for short durations.

It is a further object of the present invention to provide a method and an apparatus to completely inactivate a variety of microorganisms using supercritical fluid carbon dioxide.

BRIEF SUMMARY OF THE INVENTION

Provided is a method and apparatus for sterilizing materials, especially polymeric materials, for use in drug delivery and other biomedical application, wherein the material is treated with supercritical fluid carbon dioxide at, for example, a pressure of about 20.5 MPa (205 bar), at temperatures generally between about 25 and 40° C., for durations between about 0.6 and 4 hours. Agitation, pressure cycling, and the presence of water were found to enhance the sterilization method, which promotes diffusion of the supercritical fluid carbon dioxide into the cells of the microorganism, thereby altering the pH within the cells and killing them. The magnitude and frequency of the pressure cycling, as well as the process time and temperature, may vary according to the type and form of the material to be sterilized and the type of organisms to be killed.

DETAILED DESCRIPTION OF THE INVENTION

The methods and apparatus disclosed herein are used to sterilize biomedical materials, such as polymers, using supercritical fluid carbon dioxide. As used herein, sterilization refers to killing at least $10^6$ organisms, and more preferably $10^8$ organisms, or greater than 99.9999% of those present. Viability of cells is determined using standard techniques known in the art.

The residence time and experimental conditions required for complete sterilization are highly dependent on at least three factors. The first factor is the nature of the cell wall—that is, its chemical nature and cell shape. For example, the cell wall of the Gram-negative organisms is more fragile and less resistant to excess internal pressure that the Gram-positive organisms. The second factor is the contact between the supercritical or near supercritical carbon dioxide phase and the solid "cell phase." This contact relates to the efficiency of mass transfer between the phases. The third factor is the presence of a small amount of water.

I. Biomedical Materials and Products

The method can be used to sterilize a variety of materials, such as polymers. The method is especially useful in the sterilization of microparticles for controlled drug delivery; polymeric implants for use as prosthetics, catheters, and other indwelling devices; and materials having polymeric coatings. Polymers can be natural or synthetic, non-biodegradable or degradable. The method is particularly useful with polymers that degrade hydrolytically, especially thermally labile polymers. One preferred biocompatible polymer is polylactide-co-glycolide (PLGA). PLGA has been used extensively in the medical industry as a carrier of pharmaceuticals, in surgical sutures, and in tissue engineering applications as a biodegradable scaffolding.

Non-polymeric materials, including drugs alone or encapsulated in the polymeric material, also can be sterilized using supercritical fluids. Even drugs that are hydrolytically labile may be sterilizable using the supercritical fluid methods described herein in the substantial absence of water.

II. Microorganisms to Be Killed

Figure 1:
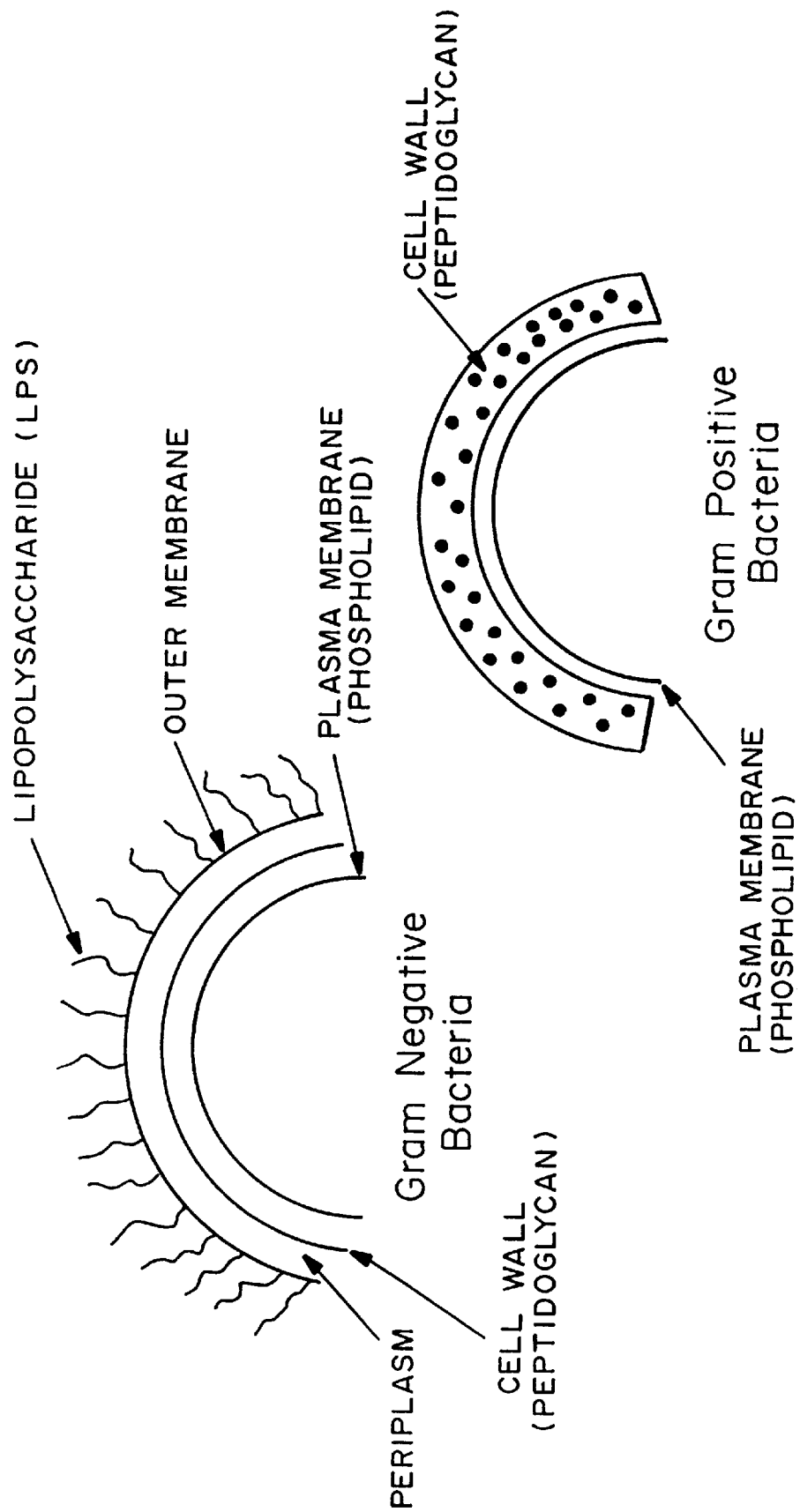
FIG. 1 is a schematic diagram of the cell wall of typical Gram-negative and Gram-positive bacteria.

The method can be used to sterilize a wide variety of microorganisms, including both Gram-negative and Gram-positive bacteria. FIG. 1 illustrates the differences in cell walls of Gram-negative and Gram-positive bacteria. The Gram-negative bacteria has an outer and inner membrane. The outer membrane is composed of lipopolysaccharides (LPS) and serves as a protective barrier to the cell. The peptidoglycan cell wall is very thin in Gram-negative bacteria. The Gram-positive bacteria has no outer membrane, but has a very thick, heavily crosslinked peptidoglycan membrane, which renders this type of cell mechanically stronger and more resistant to lysis through osmotic pressure differentials. Although the peptidoglycan layer of the Gram-positive bacteria cell is much thicker than that of the Gram-negative bacteria, most chemicals can still readily penetrate this barrier.

The method has been shown to provide complete sterilization of the following bacteria: *Bacillus cereus, Listeria innocua, Staphylococcus aureus, Salmonella salford, Psuedomonas aeruginosa, Escherichia coli, Preoteus vulgaris, Legionella dunnifii*. These bacteria were selected for testing because of their relevance in commonly found medical contamination and/or their resistance to inactivation. Table 1 describes some physical properties of these bacteria and lists infections or disorders caused by each. Sterilization of other bacteria should be readily achieved by applying the methods and teachings herein.

TABLE 1

Bacteria to Be Sterilized

| Bacteria | Physical Properties | Infections or Disorders Caused by the Bacteria |
|---|---|---|
| *Bacillus cereus* | Gram-positive, rod or cocci shape, anaerobic spores | eye infections; tuberculosis; ulcerated wounds; ear and urinary infections |
| *Listeria innocua* | Gram-positive, rod shape, aerobic | food poisoning; meningitis; and spontaneous abortion |
| *Staphylococcus aureus* | Gram-positive, cocci shape, anaerobic | chief cause of wound infections, boils, and other skin infections; abscesses in bones and other tissue |
| *Salmonella salford* | Gram-negative, rod shape, aerobic | gastroenteritis; similar structure causes typhoid fever |
| *Pseudomonas aeruginosa* | Gram-negative, rod shape, aerobic | septicemia; burn pathogen; wound infections; and a variety of hospital acquired infections |
| *Escherichia coli* | Gram-negative, rod shape, aerobic | intestinal and urinary tract infections; meningitis |
| *Preoteus vulgaris* | Gram-negative, rod shape, aerobic | very similar in structure to *Rickettsia reckettsii* which causes epidemic typhus; used as vaccine |
| *Legionella dunnifii* | Gram-negative, rod shape, aerobic | Legionnaire's disease (infection from airborne spread of the bacteria and can cause pneumonia) |

III. Process and Apparatus for Sterilization

A. Supercritical Fluid

The preferred supercritical fluid for the methods described herein is carbon dioxide. Industrial grade, 99.95% pure, carbon dioxide was found to be effective in the method. Experiments using supercritical fluid tetrafluoroethane, which has critical properties similar to carbon dioxide, but which has different chemical properties and molecular size, resulted in no measurable reduction in viable cells. Similarly, experiments using nitrogen gas at the same process conditions for supercritical fluid carbon dioxide also did not work. Accordingly, effective sterilization using the method disclosed herein is believed to require not only the enhanced mass transfer properties associated with near critical fluids, but also the specific chemical and/or physical properties of carbon dioxide. Therefore, while other supercritical fluids having comparable critical properties may be used in combination with carbon dioxide, pure carbon dioxide is preferred. The supercritical fluid or mixture preferably is used near its critical point in order for the fluid to exhibit the qualities of liquid-like density and gas-like viscosity and diffusivity, which render the fluid ideal for mass transport.

It has been suggested that the microbiocidal activity of high pressure carbon dioxide is due to the penetration of the carbon dioxide into the microbes, which lowers the internal pH to a lethal level, in contrast to other acids like phosphoric or hydrochloric acid, which do not easily enter microbial cells. See Hass, supra, p. 263; see also Kumagai, et al., "CO$_2$ Sorption by Microbial Cells and Sterilization by High-pressure CO$_2$," *Biosci. Biotech. Biochem.*, 61(6): 931–35 (1997) (investigating the correlation between carbon dioxide sorption into microbial cells and sterilization in cell-water systems). Another theory is that the excess carbon dioxide specifically inhibits decarboxylases, thereby breaking the metabolic chain. Hass, supra, p. 263.

B. Sterilization Apparatus

Figure 2:
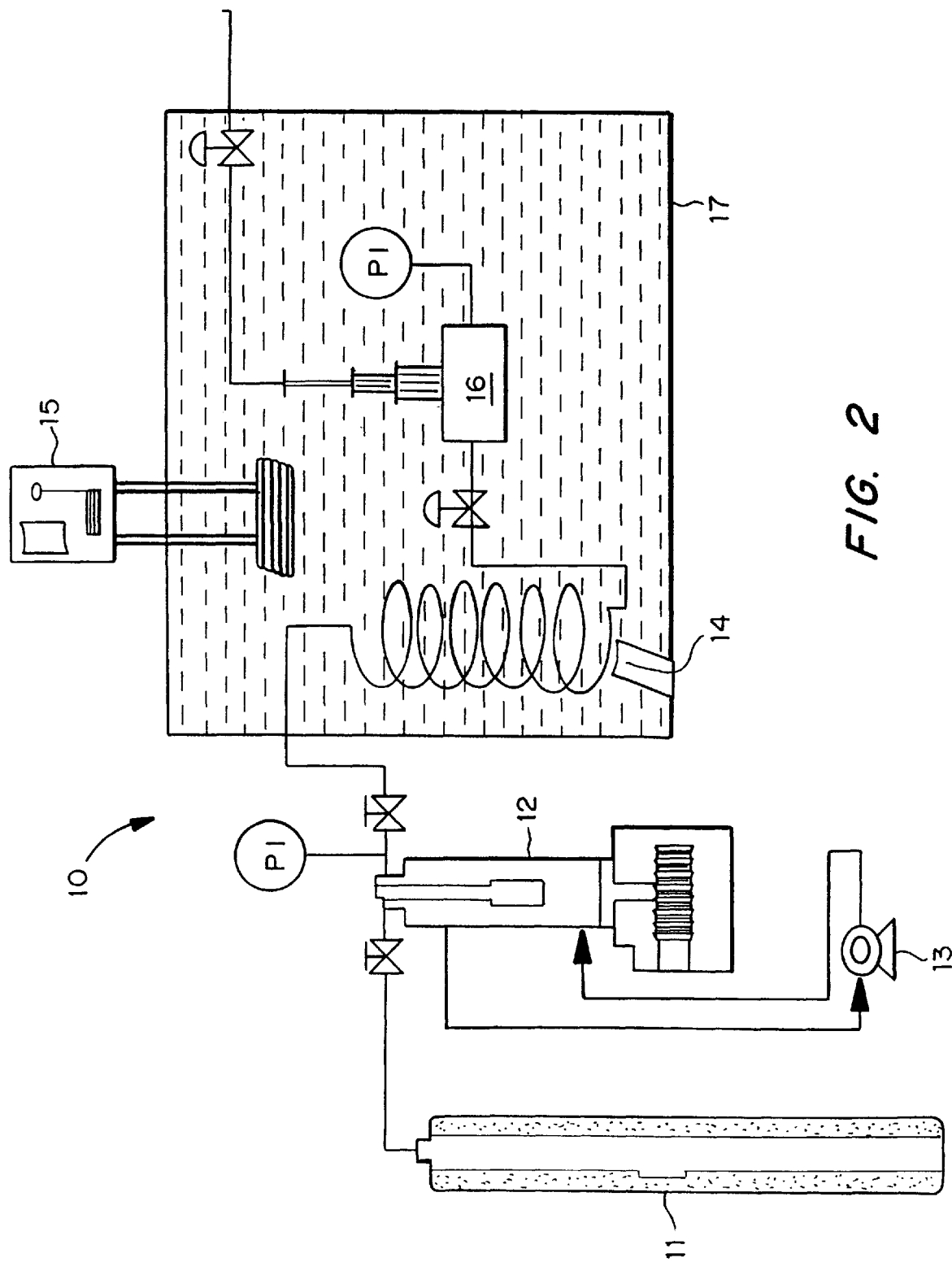
FIG. 2 is a schematic diagram of one embodiment of the sterilization apparatus.

One embodiment of the apparatus that can be used in the method is shown in FIG. 2. This apparatus 10 includes a standard compressed gas cylinder 11 containing carbon dioxide, a syringe pump 12, a pump header heat exchanger 13, a preheating coil 14, a heater 15, an extraction vessel 16, and a water bath 17.

This extraction vessel 16 is constructed of 316 stainless steel and has a total internal volume of 17 ml. However, the design, construction, and use of larger volume vessels is anticipated, for example in commercial applications, and should readily be achieved by one of skill in the art. It is also contemplated that one skilled in the art may use in the apparatus other process equipment and/or configurations to heat, cool, and pump the process media and carbon dioxide.

The extraction vessel should be designed such that continual pressurization/depressurization (pressure cycling) may be conducted without loss of media and without contamination of pressure lines via back diffusion. For example, the vessel used in the experiments described below was designed in an upside-down "T" configuration with the bottom section having a wide cylindrical configuration, having an inlet valve near the top for the introduction of fresh carbon dioxide. The top perpendicular section of the vessel is a long thin tube having an outlet valve at the top end for depressurization.

The extraction vessel also should include a filtering means, such as a 0.5 micron filter, placed before the outlet valve to ensure that none of the material to be sterilized is lost with the gas during depressurization of the extraction vessel. The extraction vessel should include an opening for introducing and removing the material to be sterilized. That opening should be capable of being selectively sealed as part of the operation of the apparatus.

C. Operation of the Apparatus

With reference to FIG. 2, the operation of the apparatus 10 includes, for example, the following steps:

(a) charging the extraction vessel 16 with the material to be sterilized;

(b) activating the constant temperature control means (e.g., the water bath 17 and/or heater 15) at the selected sterilization temperature;

(c) introducing carbon dioxide at the desired temperature and pressure into the extraction vessel 16 by pumping carbon dioxide from the gas cylinder 11 with syringe pump 12, passing the carbon dioxide through the preheating coil 14 and the pump header heat exchanger 13;

(d) agitating the contents of the extraction vessel;

(d) partially depressurizing and repressurizing (i.e. pressure cycling) the extraction vessel multiple times throughout the selected duration of the sterilization process; and (e) at the end of the processing time, ceasing agitation, depressurizing the extraction vessel, and removing the sterilized material.

In an embodiment preferred for use with non-hydrolytically labile drugs, water in an amount effective to enhance sterilization is introduced with the material to be sterilized in step (a) or with the carbon dioxide in step (c).

It is expected that the operation of the sterilization apparatus may be varied depending on the configuration and process equipment selected for the apparatus and the particular process conditions. For example, one of skill in the art may readily optimize the process equipment and controls which provide the pressure cycling, temperature control, and/or flow of fluids in and out of the reactor. The process steps may be controlled, and automated, using a programmable computer controller in communication with the sterilization apparatus.

D. Process Temperature and Pressure

The temperature of the supercritical fluid should be sufficiently near the critical point to take advantage of the enhanced mass transfer properties of supercritical fluids. Additionally, the temperature should be low enough to avoid or minimize damage to the drug or other components of the product to be sterilized, yet high enough to effect the desired sterilization. Temperatures between about 25 and 40° C. are preferred for inactivation of most microorganisms. At a pressure of 20.5 MPa (205 bar) for 4 hours or less, these temperatures were found to be sufficient to completely sterilize each of the bacteria listed in Table 1, except for *Bacillus cereus*, for which a temperature of 60° C. was required for complete sterilization.

The preferred pressure for use with carbon dioxide is about 20.5 MPa (205 bar). Lower or higher pressures may be used in the process with correspondingly higher or lower critical temperatures. Pressure cycling is believed to enhance sterilization by providing a driving force for mass transport across the cell wall. The pressure differential used in pressure cycling from a "hold" pressure of 205 bar preferably is greater than or equal to about 14 MPa (140 bar or 2000 psig). For different hold pressures, the pressure, when cycling, preferably is reduced by at least about 75% from the hold pressure. The pressure cycling preferably occurs multiple times during the process time. Increasing the frequency of the pressure cycling should reduce the time required to effect sterilization at a given set of process conditions. One of skill in the art can readily optimize the magnitude (i.e. the ΔP) and the frequency of the pressure cycling.

E. Agitation

Agitation of the process media in the extraction vessel is preferred. Intermittent manual shaking using 2 mm glass beads was found to be effective. However, other mixing means and devices, such as motorized agitators or other mixing devices, should be also be effective. In fact, continuous agitation is preferred, as it should reduce the time required to effect sterilization, as compared to intermittent agitation.

The method of agitation selected should be compatible with the material to be sterilized. For example, an impeller should be designed and operated so as to avoid damaging polymer particles or devices being sterilized.

F. Water

The presence of a small amount of water generally is preferred in the sterilization process described herein. However, water should be avoided or minimized when sterilizing materials, such as hydrolytically labile drugs and/or polymers, which may be damaged or rendered less effective by exposure to water.

Water was found to reduce the process time required for complete sterilization of *E. coli* (see Example 5 below). Water may be required for the complete sterilization of some other microorganisms. See Gilbert, et al., *Appl. Microbiology* 12:496 (1964) (showing that gaseous ethylene oxide is effective in inactivating Bacillus subtilis and Staphylococcus aureus only in the presence of moisture or if the cells have been wetted). It is believed that water enhances the sterilization process in two ways. First, water increases the permeability of the cell wall so that the carbon dioxide can more readily diffuse through the lipoprotein barrier, thereby altering the pH within the cells, killing them. Additionally, water and carbon dioxide react to form carbonic acid, which further reduces the pH within the cells. Those of skill in the art can readily optimize the amount of water required for complete sterilization of particular materials.

The water may be added separately, admitted with the carbon dioxide, or present in the pores or on the surface of the polymeric material, for example, as a result of exposure to high humidity ambient air. Larger polymeric implants simply may be prewetted prior to introducing the implant into the sterilization apparatus.

EXAMPLE 1

Sterilization of E. coli

Conditions for inactivating E. coli were evaluated to optimize the mass transfer kinetics.

Equipment

The sterilization apparatus included a custom made high pressure extraction vessel (also called the reactor) was constructed using 316 stainless steel and has an internal volume of approximately 17 ml. It was equipped with a pressure gauge to monitor internal pressure. Two high pressure valves (Whitey) served as reactor inlet and outlet points. A 0.5 $\mu$m filter was placed just prior to the outlet valve to eliminate sample loss. The extraction vessel was enclosed in a heated water bath, which was heated to the desired temperature ($\pm 1/5°$ C.). Glass beads were placed at the bottom of the reactor. The apparatus included a high pressure syringe pump (ISCO 260D) and is shown in FIG. 2 and further described above.

Procedure

Fresh E. coli (W3110 (wild type)) were cultured daily. A small volume of the bacteria in its nutrient broth (luria broth +0.1% glucose) was placed in the extraction vessel. The extraction vessel was then placed in the water bath and quickly brought to the desired temperature. Carbon dioxide was then charged into the extraction vessel through the inlet valve. The pressure was increased to 3000 psig, and then partially depressurized to 1000 psig or less. This pressure cycling was repeated. The extraction vessel was then pressurized to 3000 psig and held at the desired temperature for the given residence time. Intermittent manual shaking was used to agitate the vessel contents. After the desired residence time, the extraction vessel was quickly depressurized to atmospheric pressure and the liquid contents collected without sample loss. The experiments were repeated, varying the process pressure, temperature, and duration.

Results

Figure 3:
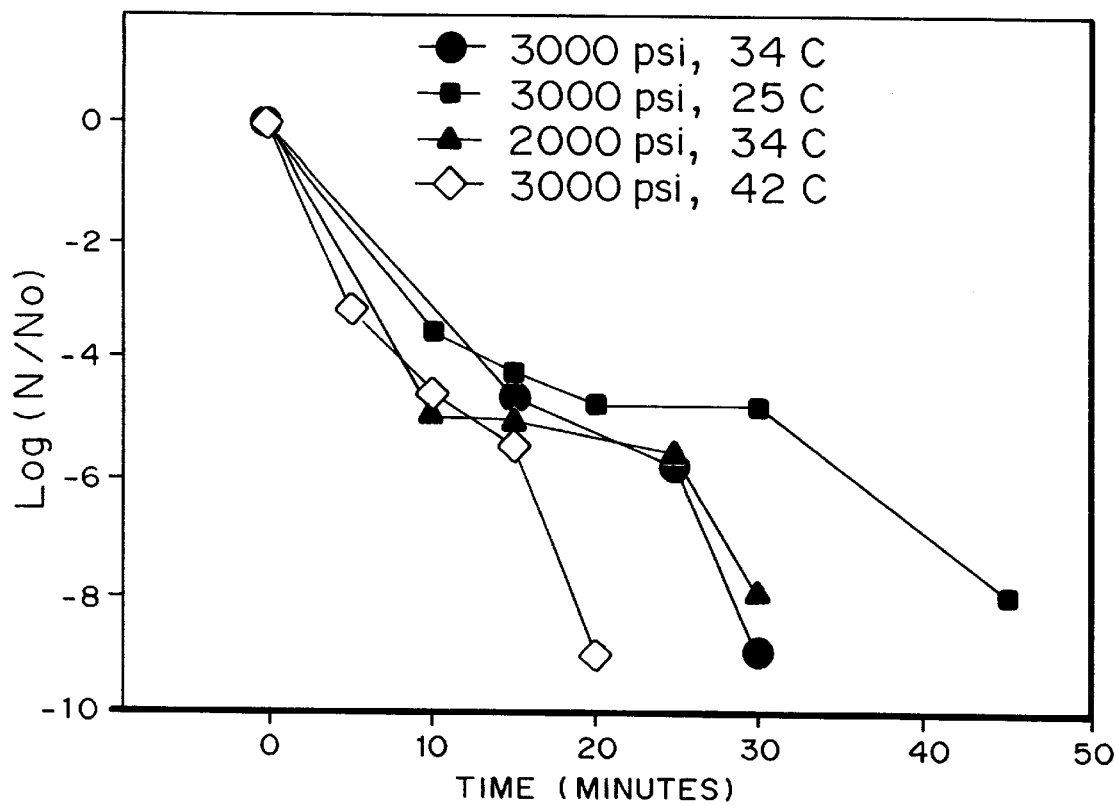
FIG. 3 is a graph showing the inactivation of *E. coli* as a function of time, using carbon dioxide at various reactor temperatures and pressures.

FIG. 3 illustrates the inactivation of E. coli as a function of time, at various process temperatures and pressures. The sterilization effect was evaluated by determining the ratio of the number of living cells after treatment to those initially added to the sterilization apparatus ($N/N_0$). Triplicate cultures were plated for average values of counted colonies for each data point. In all experiments, the initial loading of E. coli was between $10^8$ and $10^9$ CFU/ml. The final data point of each experiment represents the sample which formed no colony forming units after 48 hours of incubation. Even at subcritical conditions (i.e. temperature=25° C.), the time required for complete sterilization occurred in 60 minutes. However, at 42° C., complete sterilization occurred in less than 20 minutes.

Control experiments were conducted under identical conditions using nitrogen in place of carbon dioxide. Under these conditions, nitrogen did not exhibit the special near-critical mass transport properties of carbon dioxide. There was no reduction in the number of living cells in the control experiments, i.e. no sterilization.

EXAMPLE 2

Sterilization of PLGA Microspheres and PLA

Using the equipment and procedure in Example 1, experiments were conducted with the addition of (50:50) PLGA microspheres. Experiments were carried with 1, 7, and 20 $\mu$m solid microspheres, and with 10 $\mu$m porous microspheres and E. coli.

The 1 micron microspheres were prepared by a supercritical fluid anti-solvent technique, in which the PLGA (50:50, RG504, Boehringer Inglemheim) was precipitated from an acetone solution at 5° C. using carbon dioxide as the anti-solvent. At the beginning of each experiment carbon dioxide was pumped into the precipitation chamber (Jerguson Sight Gauge Series 32) at the desired operating temperatures using a syringe pump (ISCO Model 260D). The precipitation chamber was immersed in a temperature-controlled water bath to maintain the desired operating temperatures. The acetone/PLGA solution was injected into the chamber through a 1/32 inch O.D.×180 $\mu$m I.D. stainless steel nozzle which was inserted inside a 1/16 inch O.D.×1020 $\mu$m I.D. stainless steel tube (Alltech). The pressure was monitored by a Sensotec pressure transducer (model THE/5050-04) connected to a Sensotec pressure indicator. The PLGA/acetone solution was pumped into the chamber using a solvent delivery unit (Waters pump 6000A). Carbon dioxide was continuously flowed through the chamber and controlled by a metering valve (Whitey, SS-21RS4) in the effluent stream. The valve was heated to prevent dry ice formation, due to carbon dioxide expansion, which might block the valve. The precipitated samples were then washed and dried by passing fresh carbon dioxide at constant pressure through the apparatus for at least 30 minutes. After washing, the chamber was gradually depressurized and the sample removed. The samples were then gold coated and the size and morphology of the precipitated polymer was analyzed.

The 7 and 20 micron solid microspheres and the 10 micron porous microspheres were prepared using a single emulsion solvent evaporation method. One gram of PLGA (50:50, RG504, Boehringer Inglemheim) was dissolved in 40 ml methylene chloride and added to 2 L of an aqueous poly(vinyl alcohol) solution (1% w/v) and homogenized. Particle size was controlled by varying the homogenizer speed in the range of 5,000–10,000 rpm. The resulting dispersion was stirred for 3 hours until the methylene chloride was completely evaporated and the particles hardened. The particles were then collected by centrifugation, washed three times with distilled water, and freeze-dried for 48 hours. Particle sizing was performed using a Coulter Multisizer (Coulter Electronics, Luton, England).

The PLGA microspheres were incubated in the E. coli broth ($10^9$ CFU/ml) overnight. The PLGA/E. coli broth was introduced into the sterilization apparatus simultaneously.

The results indicate that inactivation kinetics were unaffected by the presence of the polymer and that complete sterilization of the PLGA microspheres was accomplished in 30 minutes, at 205 bar and 34° C. Analysis using scanning electron microscopy (SEM) (Hitachi 4500) showed no apparent morphological change in the microspheres following sterilization.

Samples of PLGA and poly(lactic acid) (PLA) also were subjected to the sterilization process and examined for chemical changes. Fourier-Transform Infrared Spectroscopy (FTIR), Gel Permeation Chromatography (GPC), and Differential Scanning Calorimetry (DSC) analysis showed no chemical changes in either the PLGA or PLA samples following the sterilization procedure, when compared to untreated samples.

EXAMPLE 3

Inactivation of Various Microorganisms

Using the equipment and procedure in Example 1, *Bacillus cereus, Listeria innocua, Staphylococcus aureus, Salmonella salford, Psuedomonas aeruginosa, E. coli, Preoteus vulgaris, Legionella dunnifii* were inactivated using carbon dioxide at a pressure of 205 bar, while varying other method parameters. *Bacillus cereus, Listeria innocua, Staphylococcus aureus, Salmonella salford, Psuedomonas aeruginosa, Preoteus vulgaris*, and *Legionella dunnifii* were obtained from the Australian Government Analytical Laboratory, while *E. coli* was obtained from the Biochemical Engineering Laboratory of University of New South Wales (Australia).

In all experiments, the reactors were loaded with at least $10^7$ to $10^9$ CFU/ml of the microorganisms, with the exception of the Legionella, which was difficult to culture in higher concentrations. The bacteria were cultivated in a medium containing 30 g/L typtone soya broth (code: CM129) and incubated for 18–20 hours at 37° C. *B. cereus* spores were suspended from colonies on selective agar. *Legionella dunnifii* was cultivated in a medium containing Legionella CYE Agar Base (code: CM655) and Legionella BYCE Growth Supplement (code: SR110) and incubated for 7 days at 37° C. on a petri-dish. All cells were grown daily for experiments to ensure that cells were fresh and fully grown.

Experiments were conducted varying the temperature, process time, and the number of pressure cycles. The degree of inactivation was calculated as described in Example 1. The results are provided in Table 2.

SEM analysis of the bacteria before and after treatment show that the cell walls remain largely unchanged, and are consistent with the theory that the mechanism of inactivation involves diffusion of the supercritical fluid carbon dioxide into the cells of the microorganism, thereby altering the pH within the cells to kill them. However, more defects of the cell wall are found in Gram-negative cells after the sterilization process indicating lysis in some cells. Nonetheless, the dominate inactivating mechanism is believed to be by lethal pH reduction within the cells caused by the intracellular presence of supercritical fluid carbon dioxide, since sterilization is achieved in many cases without apparent rupture of the cell wall according to SEM analysis. Lower osmotic pressure is generally required to rupture the cell wall of the Gram-negative bacteria than that of Gram-positive bacteria.

TABLE 2

The effect of $CO_2$ at 205 bar on the inactivation of various microorganisms

| Microorganism | Temp. (° C.) | Time (hrs) | Cycles (no.) | Initial CFU/mL | Degree of Inactivation |
|---|---|---|---|---|---|
| *B. cereus* | 34 | 0.6 | 3 | $5.1 \times 10^7$ | 2 Log |
| " | 34 | 2 | 6 | $5.7 \times 10^7$ | 1 Log |
| " | 60 | 2 | 6 | $5.2 \times 10^7$ | 5 Log |
| " | 60 | 4 | 6 | $1.8 \times 10^8$ | 8 Log |
| *Listeria innocua* | 34 | 0.6 | 3 | $5.8 \times 10^9$ | 3 Log |
| " | 34 | 0.6 | 6 | $2.1 \times 10^9$ | 9 Log |
| *Staphylococcus aureus* | 34 | 0.6 | 3 | $2.5 \times 10^9$ | 3 Log |
| *Staphylococcus aureus* | 34 | 0.6 | 6 | $1.2 \times 10^9$ | 7 Log |
| *Staphylococcus aureus* | 40 | 2 | 6 | $6.7 \times 10^8$ | 6 Log |
| *Staphylococcus aureus* | 40 | 4 | 6 | $1.9 \times 10^9$ | 9 Log |
| *Salmonella salford* | 34 | 0.6 | 3 | $1.5 \times 10^9$ | 3 Log |
| " | 34 | 0.6 | 6 | $1.0 \times 10^9$ | 3 Log |
| " | 40 | 2 | 6 | $6.0 \times 10^8$ | 6 Log |
| " | 40 | 4 | 6 | $2.2 \times 10^9$ | 9 Log |
| *Pseudomonas aeruginosa* | 34 | 0.6 | 3 | $7.4 \times 10^8$ | 6 Log |
| *Pseudomonas aeruginosa* | 40 | 1.5 | 6 | $2.9 \times 10^8$ | 6 Log |
| *Pseudomonas aeruginosa* | 40 | 4 | 6 | $2.4 \times 10^8$ | 8 Log |
| *E. coli* | 34 | 0.5 | 3 | $6.4 \times 10^8$ | 8 Log |
| *Proteus vulgaris* | 34 | 0.6 | 3 | $9.1 \times 10^8$ | 8 Log |
| *Legionella dunnifii* | 40 | 1.5 | 6 | $6.7 \times 10^4$ | 4 Log |

EXPERIMENT 4

Tetrafluoroethane as the Supercritical Fluid

Example, as described in Examples 1 and 3 above were conducted, with tetrafluoroethane ($T_c$=55° C.; $P_c$=40.6 atm) used in place of carbon dioxide. The experiments were conducted at 38° C. and 110 bar for 45 minutes. Measurements indicated no reduction in the number of viable cells 45 minutes. In contrast, experiments using carbon dioxide at these conditions resulted in 100% inactivation.

EXPERIMENT 5

Sterilization of "Dry" *E. Coli*

To test the importance of water in the process, *E. coli* cultures were prepared and treated to the sterilization process described herein. First, the *E. coli* cultures were centrifuged for 4 minutes at 14,000 rpm, and the supernatant decanted. The cells were then dried in vacuum for up to 8 hours. Subsequently, a first sample was subjected to the sterilization process at 35° C. at 205 bar for 2.5 hours, using carbon dioxide containing less than 100 ppm water. One hundred percent inactivation was achieved. To the second sample (prepared identically to the first) one milliliter of water was added, and the number of viable cells was determined to be $6.45 \times 10^8$ CFU/ml.

Figure 4:
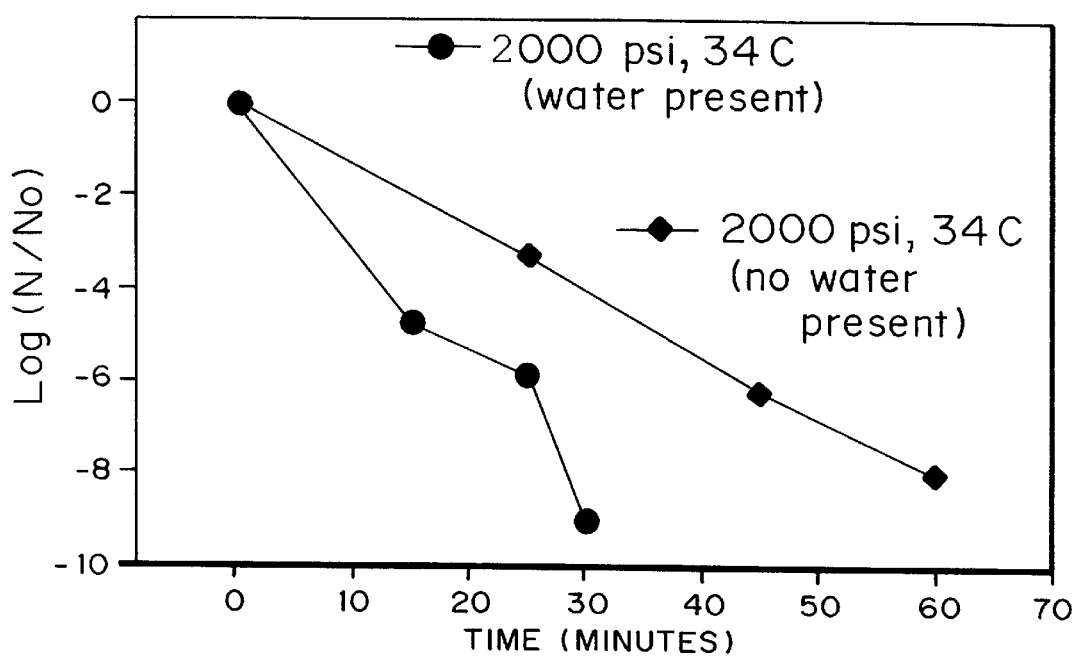
FIG. 4 is a graph showing the inactivation of *E. coli* as a function of time, comparing the sterilization kinetics at 34° C. and 2000 psig (14 MPa) in the presence and absence of water.

In a separate experiment, dry *E. coli* samples, prepared as described above and having an initial concentration of $7 \times 10^8$ CFU/ml, were subjected to the sterilization process at 35° C. at 205 bar. Cell viability was measured after 25 minutes, 45 minutes, and 60 minutes, and found to be $8 \times 10^5$ CFU/ml, $5.2 \times 10^2$ CFU/ml, and 0 CFU/ml, respectively. In contrast, "wet" *E. coli* treated at 35° C. at 205 bar was shown to be completely sterilizable in at least 30 minutes—half the time required for the "dry" samples. See FIG. 4, which graphically illustrates this comparison between sterilization of wet and dry samples.

Publications cited herein and the material for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method for sterilizing polymeric materials for medical applications comprising:
   (a) introducing the polymeric material to be sterilized into a reactor, wherein the material potentially includes bacteria to be inactivated;
   (b) charging the reactor with an effective amount of carbon dioxide;
   (c) pressurizing the reactor to an initial pressure approximately supercritical for the carbon dioxide at a temperature of less than about 60° C.;
   (d) cycling the pressure in the reactor by changing the pressure from the initial pressure to one or more higher or lower pressures followed by returning the pressure to or about the initial pressure; and
   (e) maintaining the temperature and pressure at about the initial pressure for a period of time effective to achieve a degree of inactivation of the bacteria if present exceeding 6 log orders.

2. The method of claim 1 wherein the temperature and pressure are maintained for a period of time between about 0.4 hours to about 4 hours to inactivate the bacteria.

3. The method of claim 1 wherein the material is in a form selected from the group consisting of microparticles, implants, and coatings.

4. A method for sterilizing materials for medical applications comprising:
   (a) introducing a polymeric material to be sterilized into a reactor wherein the material potentially includes bacteria to be inactivated;
   (b) charging the reactor with an effective amount of carbon dioxide;
   (c) increasing the pressure inside the reactor to between about 13 MPa and about 21 MPa, while maintaining the temperature of the reactor contents in a range between about 30° C. and about 60° C.;
   (d) cycling the pressure inside the reactor by decreasing or increasing the pressure by an amount between about 0.7 MPa and about 17 MPa, followed by returning the pressure to between about 13 MPa and about 21 MPa; and
   (e) maintaining the temperature between about 30° C. and about 60° C. and pressure between about 13 MPa and about 21 MPa for a period of time effective to achieve a degree of inactivation of the bacteria if present exceeding 6 log orders.

5. The method of claim 1 further comprising introducing water into the reactor in an amount effective to enhance sterilization of the material.

* * * * *